US008946114B2

(12) United States Patent
Nikrad et al.

(10) Patent No.: US 8,946,114 B2
(45) Date of Patent: *Feb. 3, 2015

(54) STABLE FERROUS-FERRIC NITRATE SOLUTIONS FOR FISCHER-TROPSCH CATALYST PREPARATION (75) Inventors: Pandurang V. Nikrad, Boulder, CO (US); Jesse W. Taylor, Westminster, CO (US); Richard A. Bley, Longmont, CO (US); Danny M. Dubuisson, Longmont, CO (US); Sara L. Rolfe, Loveland, CO (US); Belma Demirel, Longmont, CO (US); Dawid J. Duvenhage, Evergreen, CO (US); Harold A. Wright, Longmont, CO (US)

(73) Assignee: Res USA, LLC., Commerce City, CO (US)

( * ) Notice: Subject to any disclaimer, the term of this patent is extended or adjusted under 35 U.S.C. 154(b) by 244 days.

This patent is subject to a terminal disclaimer.

(21) Appl. No.: 12/474,440

(22) Filed: May 29, 2009

(65) Prior Publication Data

US 2009/0298681 A1   Dec. 3, 2009

Related U.S. Application Data (60) Provisional application No. 61/058,104, filed on Jun. 2, 2008.

(51) Int. Cl.
*B01J 21/08* (2006.01)
*C09K 3/00* (2006.01)
(Continued)

(52) U.S. Cl.
CPC ............... *B01J 35/002* (2013.01); *B01J 23/002* (2013.01); *B01J 23/745* (2013.01); *B01J 23/78* (2013.01);
(Continued)

(58) Field of Classification Search
CPC .... C01B 21/38; C01B 21/48; C01B 21/0622; C01G 1/08; C10G 2/332; C07C 1/044; C07C 1/0445; B01J 23/745; B01J 23/78; B01J 37/03; B01J 37/10; B01J 23/002; B01J 35/002; B01J 2523/13; B01J 2523/17; B01J 2523/41; B01J 2523/842
USPC ............ 502/182.33, 243, 258, 328, 331, 336, 502/338
IPC ....................................................... B01J 21/08
See application file for complete search history.

(56) References Cited

U.S. PATENT DOCUMENTS 2,716,631 A * 8/1955 Bechtel ......................... 203/13
4,874,888 A   10/1989 Shiomi
(Continued)

FOREIGN PATENT DOCUMENTS

JP   0545615   * 12/1993
JP   05345615    12/1993
(Continued)

OTHER PUBLICATIONS

English translation of JP-05345615, Dec. 1993.*
(Continued)

*Primary Examiner* — Jun Li
(74) *Attorney, Agent, or Firm* — Timothy S. Westby; Porter Hedges, LLC (57) ABSTRACT

A method of producing stable ferrous nitrate solution by dissolving iron in nitric acid to form a ferrous nitrate solution and maintaining the solution at a first temperature for a first time period, whereby the Fe(II) content of the ferrous nitrate solution changes by less than about 2% over a second time period. A method of producing stable Fe(II)/Fe(III) nitrate solution comprising ferrous nitrate and ferric nitrate and having a desired ratio of ferrous iron to ferric iron, including obtaining a stable ferrous nitrate solution; dissolving iron in nitric acid to form a ferric nitrate solution; maintaining the ferric nitrate solution at a second temperature for a third time period; and combining amounts of stable ferrous nitrate solution and ferric nitrate solution to produce the stable Fe(II)/Fe(III) nitrate solution. A method of preparing an iron catalyst is also described.

21 Claims, 4 Drawing Sheets (51) Int. Cl.

| | | |
|---|---|---|
| *B01J 23/745* | (2006.01) | |
| *B01J 21/06* | (2006.01) | |
| *B01J 35/00* | (2006.01) | |
| *B01J 23/00* | (2006.01) | |
| *B01J 23/78* | (2006.01) | |
| *B01J 37/03* | (2006.01) | |
| *B01J 37/10* | (2006.01) | |
| *C07C 1/04* | (2006.01) | |
| *C10G 2/00* | (2006.01) | |

(52) U.S. Cl.
CPC *B01J 37/03* (2013.01); *B01J 37/10* (2013.01); *B01J 2523/00* (2013.01); *C07C 1/044* (2013.01); *C07C 1/0445* (2013.01); *C10G 2/332* (2013.01)
USPC ...... 502/243; 502/182.33; 502/258; 502/328; 502/338; 502/331; 502/336

(56) References Cited

U.S. PATENT DOCUMENTS

| | | | |
|---|---|---|---|
| 5,324,335 | A | 6/1994 | Benham et al. |
| 5,504,118 | A | 4/1996 | Benham |
| 6,627,666 | B1 | 9/2003 | Pedersen |
| 7,879,756 | B2 | 2/2011 | Demirel et al. |
| 8,138,115 | B2 * | 3/2012 | Demirel et al. ............... 502/331 |
| 2002/0155044 | A1 | 10/2002 | Ciampi |
| 2004/0106517 | A1 * | 6/2004 | Dlamini et al. ............... 502/326 |
| 2004/0152791 | A1 | 8/2004 | Zyl et al. |
| 2009/0062108 | A1 * | 3/2009 | Demirel et al. ............... 502/158 |
| 2009/0069451 | A1 * | 3/2009 | Demirel et al. ............... 518/713 |
| 2009/0075814 | A1 | 3/2009 | Duvenhage et al. |

FOREIGN PATENT DOCUMENTS

| | | |
|---|---|---|
| WO | 2009023627 | 2/2009 |
| WO | 2009148952 | 12/2009 |
| ZA | 201008546 | 1/2012 |

OTHER PUBLICATIONS

International Search Report and Written Opinion dated Mar. 2, 2010, issued in corresponding Application No. PCT/US09/45634, 11 pages.
Office Action issued Aug. 3, 2012 in counterpart Chinese Patent Application No. 200980129296.4 and English Translation, (23 pages).
Office Action issued in counterpart Eurasian Patent Application No. 201071265 and English Translation, (4 pages).
Supplementary European Search Report for EP Application No. 09759112.7 dated Nov. 22, 2011, pp. 1-7.
Chinese Office Action dated Jan. 31, 2013 for corresponding Chinese Application No. 200980129296.4 (10 pgs.).
Australian Examination Report dated Oct. 10, 2013 for corresponding Australian Application No. 2009256462 (3 pgs.).
Eurasian Office Action dated Oct. 15, 2013 for corresponding Eurasian Application No. 201071265/28 (5 pgs.).
Eurasian Office Action dated Mar. 25, 2013 for corresponding Eurasian Application No. 201071265/28 (5 pgs.).
Canadian Office Action dated Mar. 26, 2013 for corresponding Canadian Application No. 2,726,365 (2 pgs.).
Canadian Office Action dated May 23, 2012 for counterpart Canadian Application No. 2726365; 3 pages.
Eurasian Office Action dated May 9, 2014 for corresponding Eurasian Application No. 201071265/28 (4 pgs.).
Canadian Office Action dated Oct. 18, 2013 for corresponding Canadian Application No. 2,726,365 (2 pgs.).
European Examination Report dated Apr. 7, 2014 for corresponding European Application No. 09759112.7 (4 pgs.).

* cited by examiner

STABLE FERROUS-FERRIC NITRATE SOLUTIONS FOR FISCHER-TROPSCH CATALYST PREPARATION

CROSS-REFERENCE TO RELATED APPLICATIONS

This application claims the benefit under 35 U.S.C. §119 (e) of U.S. Provisional Patent Application No. 61/058,104 filed Jun. 2, 2008, the disclosure of which is hereby incorporated herein by reference in its entirety.

STATEMENT REGARDING FEDERALLY SPONSORED RESEARCH OR DEVELOPMENT

Not Applicable.

BACKGROUND OF THE INVENTION

1. Field of the Invention

The present invention relates generally to iron Fischer-Tropsch catalysts. More particularly, the present invention relates to a method for preparing stable Fe(II)/Fe(III) nitrate and/or ferrous nitrate solutions to produce Fischer-Tropsch synthesis catalyst, and the catalyst produced thereby. Still more specifically, the present invention relates to a method of producing a Fischer-Tropsch catalyst by precipitating iron from an acid solution comprising a desired ratio of ferrous iron to ferric iron and wherein the acid solution is stable for a desired time period.

2. Background of the Invention

The Fischer-Tropsch (FT) technology is used to convert a mixture of hydrogen and carbon monoxide (synthesis gas or syngas) to valuable hydrocarbon products. Often, the process utilizes a slurry bubble column reactor (SBCR). The technology of converting synthesis gas originating from natural gas into valuable primarily liquid hydrocarbon products is referred to as Gas-To-Liquids (GTL) technology. When coal is the raw material for the syngas, the technology is commonly referred to as Coal-To-Liquids (CTL). The FT technology is one of several conversion techniques included in the broader GTL/CTL technology.

One of the primary difficulties encountered in using iron-based catalysts for carrying out the FT reaction in a slurry bubble column reactor (SBCR) is the breakdown of the initial catalyst particles into very small particles, i.e. less than 5 microns in size. Although the small particle size is advantageous for increasing surface area and reaction rate of the catalyst, the problem lies in separating the small catalyst particles from the wax slurry medium. Separating the catalyst particles from the wax is desired since the iron catalyst when operated under the most profitable conditions wherein wax is produced utilizes removal of the wax from the reactor to maintain a constant height of slurry in the reactor.

It is impossible to determine the actual attrition resistance that is sufficient without knowing the type of reactor system, the type of wax/catalyst separation system and the system operating conditions.

Heretofore, attempts at developing strengthened iron-based catalysts have focused on producing the strongest possible catalysts, regardless of the actual strength sufficient for a particular system. Such approaches sacrifice activity and selectivity for catalyst strength which may exceed that which is sufficient. Most of the prior art has focused on attempting to maximize strength of the catalyst without due regard for the negative impact of high levels of strengthener, e.g. silica, on activity and selectivity. Further, tests for catalyst strength have been carried out ex-situ, i.e. outside the SBCRs. Many of the tests have been conducted in a stirred tank reactor (autoclave) which subjects the catalyst to severe shearing forces not typically encountered in slurry bubble column reactors.

Improved catalyst strength can be achieved by depositing the iron on a refractory support such as silica, alumina or magnesia or by adding a structural promoter to the baseline catalyst. The challenge is to strengthen the catalyst without appreciably compromising the activity and selectivity of the catalyst.

Formation of strengthened FT iron catalysts which utilizes a desired ratio of ferric to ferrous iron in an acid solution from which precipitation of iron phase occurs has been reported in U.S. patent application Ser. No. 12/198,459 filed Aug. 26, 2008 and entitled, "Strengthened Iron Catalyst for Slurry Reactors." The disclosure of U.S. patent application Ser. No. 12/198,459 is incorporated hereby herein for all purposes not inconsistent with this disclosure. Ferrous nitrate solution is reported to be very unstable in the literature. Production of stable ferrous nitrate solutions and stable solutions comprising a desired ratio of ferrous to ferric iron is challenging, and the production thereof will lead to more consistent iron-catalyst formation and a decrease in the time and costs of catalyst formation.

Accordingly, there is a need for a method of producing stable ferrous nitrate solutions and stable nitrate solutions comprising a desired ratio of ferric to ferrous iron. Also needed is a method of producing an iron FT catalyst which incorporates the use of the stable iron nitrate solutions. Use of these methods should desirably allow production of an iron FT catalyst which has resistance against breakdown during FT reaction and also maintains high activity and selectivity toward high molecular weight hydrocarbons. A method for stabilization of Fe(II)/Fe(III) nitrate solution should enhance the rate of the catalyst manufacturing process at dissolution and/or precipitation steps, desirably increase reproducibility of catalyst manufacture.

SUMMARY

Herein disclosed is a method for producing a stable ferrous nitrate solution, the method comprising dissolving iron in nitric acid having a first nitric acid concentration to form a ferrous nitrate solution and maintaining the solution at a first temperature for a first time period, whereby the Fe(II) content of the ferrous nitrate solution changes by less than about 2 weight percent over a second time period. In embodiments, the first nitric acid concentration is in the range of from about 5 to about 10 weight percent. In embodiments, the first nitric acid concentration is about 6 weight percent. In embodiments, the first temperature is a temperature in the range of from about 25° C. to about 35° C. In embodiments, the first time period is greater than 30 minutes. In embodiments, the first time period is greater than 45 minutes. In embodiments, the method further comprises covering the ferrous nitrate solution during the first time period. In embodiments, the second time period is at least one hour. In embodiments, the second time period is at least one day. In embodiments, the second time period is at least two days. The method can further comprise filtering the stable ferrous nitrate solution. Also disclosed is a stable ferrous nitrate solution produced via the disclosed method.

Also disclosed is a method of producing a stable Fe(II)/Fe(III) nitrate solution comprising ferrous nitrate and ferric nitrate and having a desired ratio of ferrous iron to ferric iron, the method comprising: obtaining a stable ferrous nitrate solution by the method disclosed above; dissolving iron in nitric acid having a second nitric acid concentration to form a ferric nitrate solution, wherein the second nitric acid concentration is greater than the first nitric acid concentration; maintaining the ferric nitrate solution at a second temperature for a third time period; and combining amounts of stable ferrous nitrate solution and ferric nitrate solution to produce the stable Fe(II)/Fe(III) nitrate solution having the desired ratio of ferrous iron to ferric iron, wherein the Fe(II) content of the stable Fe(II)/Fe(III) nitrate solution changes by less than about 2 weight percent over a fourth time period. In embodiments, the second nitric acid concentration provides a specific gravity of the ferric nitrate solution of greater than 1.115. In embodiments, the method further comprises heating the ferric nitrate solution to a third temperature for a fifth period of time. The third temperature can be greater than the first temperature. In embodiments, the third temperature is a temperature of greater than about 70° C. In embodiments, the fifth time period is a time greater than about 40 minutes. In embodiments, the first nitric acid concentration is in the range of from about 5 to about 10 weight percent. In embodiments, the first nitric acid concentration is about 6 weight percent. In embodiments, the first temperature is a temperature in the range of from about 25° C. to about 35° C. In embodiments, the first time period is greater than 30 minutes. In embodiments, the first time period is greater than 45 minutes. In embodiments, the method further comprises covering the ferrous nitrate solution during the first time period. In embodiments, the second time period is at least one hour. In embodiments, the second time period is at least one day. In embodiments, the second time period is at least two days. The method can further comprise covering the ferric nitrate solution during the third time period. In embodiments, the fourth time period is at least one hour. In embodiments, the fourth time period is at least one day. In embodiments, the desired ratio of ferrous iron to ferric iron is about 1:3. The method can further comprise allowing the stable ferrous nitrate solution to cool to room temperature prior to combining amounts of stable ferrous nitrate solution and ferric nitrate solution to produce the stable Fe(II)/Fe(III) nitrate solution. The method can further comprise filtering the ferrous nitrate solution, the ferric nitrate solution, or both. Also disclosed is a stable Fe(II)/Fe(III) nitrate solution comprising ferrous nitrate and ferric nitrate formed according to the previously-described method.

Also disclosed is a method of producing an iron catalyst, the method comprising: obtaining a stable Fe(II)/Fe(III) nitrate solution according to the above procedure; and combining the stable Fe(II)/Fe(III) nitrate solution with a precipitating agent whereby catalyst precipitate is formed. In embodiments, the stable Fe(II)/Fe(III) nitrate solution has a desired ratio of ferrous iron to ferric iron of about 1:3. In embodiments, the precipitating agent is selected from the group consisting of $NH_4OH$, $(NH_4)_2CO_3$, $NH_4HCO_3$, $NaOH$, $Na_2CO_3$, $NaHCO_3$, $KOH$, $K_2CO_3$, $KHCO_3$, and combinations thereof. The method can further comprise co-precipitating at least one other metal or metalloid from a nitrate solution. The at least one other metal or metalloid can be selected from the group consisting of magnesium, copper, aluminum, silicon, and combinations thereof. In embodiments, the method further comprises washing the precipitate. In embodiments, the method further comprises alkalizing the precipitate with an alkaline material. The alkaline material can comprise potassium carbonate. In embodiments, the method further comprises promoting the precipitate by contacting the precipitate with a structural promoter. The structural promoter can comprise liquid potassium silicate. In embodiments, the structural promoter comprises tetraethyl ortho silicate, TEOS. Also disclosed is an iron catalyst formed by the previously-described method.

The present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

NOTATION AND NOMENCLATURE

The term "Fe(II)/Fe(III) nitrate solution" is used herein to refer to an iron nitrate solution comprising ferrous nitrate and ferric nitrate.

Unless otherwise stated, percent or % is used to refer to weight percentages.

DETAILED DESCRIPTION

I. Overview

In an FT process, a hydrogen and carbon monoxide-containing gas stream is introduced into a Fischer-Tropsch reactor which can employ a catalyst slurry using an iron-based catalyst; the catalyst slurry can comprise a precipitated iron catalyst; the precipitated iron catalyst can be promoted with predetermined amounts of potassium and copper depending on the pre-selected probability of linear condensation polymerization and the product molecular weight distribution sought.

Production of the iron FT catalyst can comprise addition of an acid solution to a base, addition of a base solution to an acid solution, or a combination thereof. The acid solution can comprise a certain ratio of ferric to ferrous iron. This disclosure provides a means for obtaining a desired ratio of ferric to ferrous iron in the acid solution, whereby the acid solution is stable for a time and maintains the desired ratio of ferric to ferrous iron.

According to literature, when iron is dissolved in nitric acid of specific gravity of 1.05, ferrous nitrate is produced, but with more concentrated acids, a mixture of ferrous and ferric nitrates is produced. With nitric acid of specific gravity of 1.115, substantially only ferric nitrate is produced.

Iron is combined with nitric acid to produce ferrous nitrate, $Fe(NO_3)_2$ according to the following equations:

$$Fe+2HNO_3 \rightarrow Fe(NO_3)_2+H_2. \tag{1}$$

$$4Fe+10HNO_3 \rightarrow 4Fe(NO_3)_2+NH_4NO_3+3H_2O. \tag{1b}$$

Ferrous nitrate is known to be very unstable and yellow oxides ($Fe_2O_3$) may be precipitated on exposure to air according to the following equation:

$$6Fe(NO_3)_2 + 5H_2O \rightarrow 3Fe_2O_3 + 2NO + 10HNO_3. \quad (2)$$

Ferrous oxidation and precipitation leads to the production of ferric hydroxide ($Fe(OH)_3$) according to the following equation:

$$3Fe(NO_3)_2 + 7H_2O \rightarrow 3Fe(OH)_3 + 5HNO_3 + NO. \quad (3)$$

With time, ferric hydroxide may be mineralized, and ferric iron oxide formed.

Ferrous iron normally can be oxidized to ferric iron in minutes, however, the time for this oxidation is dependent on pH, temperatures and the presence of other soluble ions. The lower the pH and temperature, the longer time taken for the completion of the oxidation reaction. At pH of 7.0, oxidation of Fe(II) can take 1 hour at 21° C. and 10 hours at 5° C. At pH of 6, it can take 100 hours.

With nitric acid of specific gravity at around 1.115, substantially only ferric nitrate, $Fe(NO_3)_3$, is produced, and ferric (Fe(III)) nitrate is known to be quite stable. Ferric nitrate is produced by the following reactions:

$$Fe + 3HNO_3 \rightarrow Fe(NO_3)_3 + 1.5H_2, \text{ and} \quad (4)$$

$$2Fe + 8HNO_3 \rightarrow 2Fe(NO_3)_3 + 2NO + 4H_2O. \quad (4b)$$

Herein disclosed is a ferrous nitrate solution which is stable for a desired time period of at least one hour, at least two hours, at least one day, or at least two days. Also disclosed herein is a stable Fe(II)/Fe(III) nitrate solution formed by mixing of stable ferrous nitrate solution of this disclosure with ferric nitrate solution. In embodiments, the ferrous nitrate solution and/or the Fe(II)/Fe(III) nitrate solution is stable for a period of at least one hour, at least two hours or at least one day. In embodiments, the ferrous nitrate solution and/or the Fe(II)/Fe(III) nitrate solution is stable for a period of at least two days. The stability of the solutions can be determined by the amount of Fe(II) in the solutions (ferrous nitrate solution or ferric/ferrous nitrate solution comprising both ferrous nitrate and ferric nitrate). A "stable" solution is defined herein as a solution that has a percent Fe(II) that changes by less than a desired amount (e.g. by less than about 2% or less than about 1%) over a desired time period, e.g. at least one hour, at least two hours, at least one day, at least two days, or some time therebetween. In embodiments, a stable solution has a percent Fe(II) that changes by less than 2 weight percent over a desired time period. In embodiments, a stable solution has a percent Fe(II) that changes by less than 2 weight percent over a time period of at least one day. In embodiments, a stable solution has a percent Fe(II) that changes by less than 1 weight percent over a desired time period. In embodiments, a stable solution has a percent Fe(II) that changes by less than 1 weight percent over a time period of at least one day.

To achieve a targeted Fe(II)/Fe(III) nitrate ratio, the precipitation step of iron catalyst manufacturing can be very difficult if the Fe(II)/Fe(III) nitrate solution is not stable. In unstable solutions, the Fe(II)/Fe(III) nitrate ratio may keep changing after mixing the Fe(II) and Fe(III) solutions. This can impede the subsequent precipitation process. The method herein disclosed allows stabilization of an Fe(II)/Fe(III) solution and helps maintain a targeted Fe(II)/Fe(III) ratio. This enables effective production of a consistent catalyst, sometimes in a shortened production time. Implementation of the disclosed method may provide a significant cost savings in terms of catalyst quality, material, time and/or labor in the catalyst manufacturing process.

II. Method of Stabilizing Ferrous Nitrate Solutions and/or Ferric/Ferrous Nitrate Solutions Ferrous nitrate solution will be referred to at times as ferrous nitrate solution (1); ferric nitrate solution will be referred to at times as ferric nitrate solution (2); ferric/ferrous nitrate solution comprising ferrous nitrate and ferric nitrate will be referred to at times as ferric/ferrous nitrate solution (3).

Many factors affect the Fe(II) stability in mixed Fe(II)/Fe (III) solutions. To increase stability of Fe(II)/Fe(III) mixtures, in embodiments, the mixtures are covered in order to prevent volume loss over time. To enhance reproducibility, in embodiments, acid addition is performed at a temperature of greater than about 30° C. After the acid addition step is complete, the solution can be stirred for a time, e.g. at least 45 minutes, prior to heating. This may ensure more complete dissociation of the iron metal. In embodiments, solutions that are filtered after the addition of acid are stable for at least one hour. If undissociated iron is left in the ferrous nitrate and ferric nitrate solutions, the Fe(II) content in the mixed solution (3) may be stable for a longer period of time than if the individual ferrous nitrate solution (1) and ferric nitrate solution (2) are filtered. Without wishing to be limited by theory, this may be because the amount of Fe(II) that oxidizes to Fe(III) over time is of the same magnitude as the remaining elemental iron that is oxidized to Fe(II) in the acid solution.

According to this disclosure, formation of a stable ferrous nitrate solution comprises dissolving iron in nitric acid having a first nitric acid weight percent, and maintaining the solution at a first temperature for a first period of time. The ferrous nitrate solution can be stirred during the first period of time. In embodiments, the first temperature is a temperature in the range of from about 25° C. to about 35° C. In embodiments, the first temperature is a temperature in the range of from about 30° C. to about 35° C. In embodiments, the first period of time is greater than about 30 minutes. In embodiments, the first period of time is greater than about 40 minutes. In embodiments, the first period of time is greater than about 45 minutes. In embodiments, the nitric acid used to dissolve the iron for preparation of the stable ferrous nitrate solution has a first nitric acid weight percent of about 5-10 weight percent, 6-9 weight percent, or about 6 weight percent.

In embodiments, stable ferrous nitrate solution is stable for a second time period. In embodiments, the second time period is at least one hour, at least two hours, at least one day, or at least two days. In embodiments, stable ferrous nitrate solution is stable for at least one day. In embodiments, stable ferrous nitrate solution is stable for at least two days. In embodiments, stable ferrous nitrate solution is stable for at least three days. In embodiments, the percent Fe(II) in the stable ferrous nitrate solution changes by less than about 1% over a period of about one hour, at least two hours, at least one day, or at least two days. In embodiments, the percent Fe(II) in the stable ferrous nitrate solution changes by less than about 2% over a period of about one hour, about two hours, or about one day. In embodiments, the percent Fe(II) in the stable ferrous nitrate solution changes by less than about 2% over a period of about two days. In embodiments, the ferrous nitrate solution is filtered. In embodiments, the stable ferrous nitrate solution is covered during the first time period.

Formation of ferric acid solution comprises dissolving iron in nitric acid having a second weight percent nitric acid and maintaining the solution at a second temperature for a third period of time. In embodiments, the second temperature is a temperature in the range of from about 60° C. to about 80° C. In embodiments, the second temperature is a temperature in the range of from about 60° C. to about 70° C. In embodiments, the second temperature is a temperature of about 65° C. In embodiments, the second temperature is a temperature of greater than about 70° C. In embodiments, the third period of time is a time of greater than about 30 minutes. In embodiments, the third period of time is a time of greater than about 40 minutes. In embodiments, the third period of time is a time of greater than about 45 minutes. In embodiments, the nitric acid used for dissolution of iron in preparation of ferric nitrate solution has a weight percentage of nitric acid in the range of from about 10-20 weight percent. In embodiments, the nitric acid used for dissolution of iron in preparation of ferric nitrate solution has a weight percentage of nitric acid in the range of from about 12-18 weight percent. In embodiments, the nitric acid used for dissolution of iron in preparation of ferric nitrate solution has a weight percentage of nitric acid of about 13 weight percent. In embodiments, the nitric acid is about 17 weight percent nitric acid. In embodiments, the ferric nitrate solution is filtered. In embodiments, the ferric nitrate solution is covered during the third time period.

In embodiments, forming a solution of ferric nitrate further comprises heating the ferric nitrate solution to a temperature of greater than about 70° C. In embodiments, forming a solution of ferric nitrate further comprises heating the ferric nitrate solution to a temperature of greater than about 75° C. In embodiments, forming a solution of ferric nitrate further comprises heating the ferric nitrate solution to a temperature in the range of from 35° C. to 75° C.

In embodiments, combining stable ferrous nitrate solution and ferric nitrate solution such that a stable Fe(II)/Fe(III) nitrate solution is formed having a desired ratio of ferrous to ferric iron comprises combining stable ferrous nitrate solution and ferric nitrate solution to produce a ferric/ferrous nitrate solution comprising about 20-30 weight percent ferrous iron and about 70-80 weight percent ferric iron. In embodiments, combining stable ferrous nitrate solution and ferric nitrate solution such that a stable Fe(II)/Fe(III) nitrate solution is formed having a desired ratio of ferrous to ferric iron comprises combining stable ferrous nitrate solution and ferric nitrate solution to produce a ferric/ferrous nitrate solution comprising about 22-28 weight percent ferrous iron and about 72-78 weight percent ferric iron. In embodiments, combining stable ferrous nitrate solution and ferric nitrate solution such that a stable Fe(II)/Fe(III) nitrate solution is formed having a desired ratio of ferrous to ferric iron comprises combining stable ferrous nitrate solution and ferric nitrate solution to produce a ferric/ferrous nitrate solution comprising about 25 weight % ferrous iron and about 75 weight percent ferric iron. In embodiments, the percent Fe(II) in the stable Fe(II)/Fe(III) nitrate solution changes by less than about 1 weight percent over a period of about one hour, about two hours, or about one day. In embodiments, the percent Fe(II) in the stable Fe(II)/Fe(III) nitrate solution changes by less than about 2 weight percent over a period of about one hour, about two hours, or about one day. In embodiments, the percent Fe(II) in the stable Fe(II)/Fe(III) nitrate solution changes by less than about 2% over a period of about two days. In embodiments, the ferrous nitrate solution, the ferric nitrate solution, or both are filtered prior to combining to produce the Fe(II)/Fe(III) nitrate solution.

In embodiments, a mixture of ferrous nitrate solution and ferric nitrate solution according to this disclosure is utilized to make iron-based Fischer-Tropsch catalyst. In embodiments, the desired ferrous nitrate/ferric nitrate solution comprises 20-30 weight percent (e.g. 25 weight percent) ferrous nitrate and about 70-80 weight percent (e.g. about 75 weight percent) ferric nitrate. Although the examples presented herein provide specific ratios of ferric/ferrous nitrate, the disclosed method of stabilizing ferrous nitrate solutions and ferric/ferrous nitrate solutions produced therefrom, can be used to stabilize Fe(II)/Fe(III) nitrate solutions having any desired ratio of ferric to ferrous nitrate.

Although discussed with respect to the production of iron FT catalyst, the stabilized ferrous nitrate solution and/or the stabilized ferric/ferrous nitrate solution herein disclosed may be used for purposes other than production of FT catalyst, and discussion thereof is not meant to be limiting.

III. Method of Making Iron FT Catalyst Utilizing Stabilized Ferrous Nitrate and/or Ferric/Ferrous Nitrate Solutions In embodiments, an iron FT catalyst is formed substantially according to the description in U.S. Pat. No. 5,504,118 and/or U.S. patent application Ser. No. 12/189,424, now U.S. Pat. No. 7,879,756, with the iron nitrate solutions being formed as described in this disclosure. This catalyst is made using elemental iron and optionally copper as starting materials. The disclosures of U.S. Pat. No. 5,504,118 and U.S. patent application Ser. No. 12/189,424, now U.S. Pat. No. 7,879,756, are hereby incorporated herein in their entirety for all purposes not inconsistent with this disclosure.

The first step in the preparation of the raw catalyst is dissolution of the metals in nitric acid to form a mixture of ferrous nitrate, ferric nitrate and optionally cupric or at least one other metal nitrate in appropriate proportions. In embodiments, Fe(II)/Fe(III) nitrate solution having a desired ratio of ferrous to ferric iron in the acid solution is formed as described in Section II hereinabove. Specifically, a stable ferrous nitrate solution is formed, a ferric nitrate solution is formed, and appropriate amounts of the stable ferrous nitrate and ferric nitrate solutions are combined to yield a stable ferric/ferrous nitrate solution having the desired ratio of ferric to ferrous iron.

In embodiments, the next step in the FT catalyst formation is precipitation of a catalyst precursor from the nitrate solution using a precipitating agent (base.) In embodiments, the precipitating agent (base) is selected from the group consisting of $NH_4OH$, $(NH_4)_2CO_3$, $NH_4HCO_3$, $NaOH$, $Na_2CO_3$, $NaHCO_3$, $KOH$, $K_2CO_3$, $KHCO_3$, and combinations thereof. In embodiments, the precipitating agent comprises sodium carbonate. In embodiments, the base comprises ammonium hydroxide.

Precipitation agent (e.g. base) can be added to nitrate solution, or nitrate solution added to base. In embodiments, precipitation agent (e.g. base) is added to hot nitrate solution at ambient temperature. The amount of precipitation agent (e.g. base) can be such that the pH of the solution reaches a value in the range of from about 7.0 to about 7.5, e.g. about 7.4. At this point, metals precipitate out as oxides, hydroxides, carbonates, or a combination thereof. The mixture can then be cooled (e.g., to about 80° F.) and/or the final pH adjusted. The final pH can be adjusted to a pH in the range of from about 7.0 to about 7.5, e.g. a pH of about 7.2.

Following precipitation, the catalyst precursor can be washed using high quality water which is preferably free of chlorine. The washing can be performed according to any methods known in the art. In embodiments, the slurry is introduced, e.g. pumped, from the precipitation vessel into a holding tank. The holding tank can be located upstream of a filtration apparatus, e.g. a vacuum drum filter. The catalyst precursor may be allowed to settle in the holding tank and a clear layer of concentrated solution may form above the solids. This layer may be drawn off before the slurry is washed and filtered. A vacuum drum filter fitted with water spray bars may be used for washing the catalyst precursor and concentrating the slurry. The electrical conductivity of the filtrate can be monitored to ensure complete washing of the catalyst precursor has been effected. For example, the catalyst precursor can be washed until the electrical conductivity of the filtrate is about 40, about 30, or about 20 percent or less of the original electrical conductivity.

Following washing, the precipitate (or washed precipitate) can be alkalized by any means known in the art. For example, the addition of potassium carbonate can be used to alkalize the precipitate or washed precipitate. In embodiments, alkalization is performed prior to spray drying in order to adjust the Fe:K ratio to a desired value. In embodiments, alkalization is performed prior to spray drying in order to provide a desired Fe:K ratio. For example, in embodiments, following washing of catalyst precursor, potassium carbonate is added in an amount appropriate for the quantity of iron contained in the batch. Potassium is a promoter for chain growth and may also maintain the catalyst in iron carbide form. Adding more than appropriate amount of potassium may cause formation of more oxygenated products which may oxidize the catalyst, and is generally avoided. In embodiments, potassium carbonate is added to the slurry after washing is completed and prior to spray drying. Potassium carbonate can be dissolved in a small amount of water and this solution mixed thoroughly with the catalyst precursor slurry to uniformly distribute the potassium. In embodiments, the weight percent of solid catalyst material in the slurry at this point is in the range of from about 8 to about 12.

In embodiments, as described in U.S. patent application Ser. No. 12/198,459 filed Aug. 26, 2008 and entitled, "Strengthened Iron Catalyst for Slurry Reactors," the iron FT catalyst further comprises a structural support such as a binder incorporated after precipitation of the catalyst precursor or a support material coprecipitated with iron. The support material may serve to increase the structural integrity of the catalyst. In embodiments, the iron catalyst of the present disclosure comprises coprecipitated material selected from iron, silica, magnesium, copper, aluminum, and combinations thereof. Alternatively, or additionally, potassium silicate binder, colloidal silica, and/or tetraethyl ortho silicate (TEOS) can be added to a precipitated catalyst to increase the strength thereof.

In embodiments, the structural promoter is incorporated into the iron catalyst by coprecipitation. The structural promoter and its incorporation can be as described in U.S. patent application Ser. No. 12/207,859, which is hereby incorporated herein. The iron catalyst precursor can be prepared by co-precipitation of copper, silicon, magnesium, and aluminum with iron to provide an FT catalyst that exhibits high activity, selectivity, and stability.

In embodiments, the structural promoter is added to a conventional precipitated catalyst subsequent precipitation of the catalyst precursor comprising iron hydroxides, iron oxides and/or iron carbonates. In embodiments, structural promoter is coprecipitated with the catalyst material, and additional structural promoter (e.g. binder) is added following the precipitation of the catalyst material.

In embodiments structural promoter comprising silicon is added to a catalyst precipitate, the precipitate comprising iron phases. The iron phases can include iron hydroxides, iron carbonates, iron oxides, and combinations thereof. The structural promoter can comprise potassium silicate aqueous solution, which will be referred to herein as liquid potassium silicate. In embodiments, the liquid structural promoter comprises tetraethyl ortho silicate, TEOS, or potassium silicate and is added such that the catalyst has a silica content of from about 1 wt. % to about 2.2 wt. %.

As mentioned above, in embodiments, various amounts of liquid potassium silicate ($K_2SiO_3$) are added to a raw precipitated catalyst. In embodiments, precipitated iron catalyst is impregnated by mixing thoroughly with various amounts of aqueous potassium silicate. In embodiments, the precipitate is heated to 125° C. at the rate of 2° C./min, and held at this temperature for 12 h, and then ramped to 350° C. at the rate of 1°/min, and calcined at this temperature for 16 h prior to impregnation with aqueous potassium silicate solution. In other embodiments, liquid potassium silicate is added to iron precipitate prior to spray drying of the impregnated precipitate. The iron catalyst can comprise $SiO_2$ concentrations in the range of from about 1.0 weight percent to about 2.2 weight percent. The potassium silicate solution can comprise $SiO_2$/$K_2O$ in a desired ratio for the production of catalyst having the desired composition.

Preparation of precipitated catalyst can comprise: Forming a stable solution of ferrous nitrate, forming a solution of ferric nitrate, and combining desired amounts of stabilized ferrous nitrate solution and ferric nitrate solution such that a stable Fe(II)/Fe(III) nitrate solution is formed having a desired ratio of ferrous to ferric iron.

As described in Section II hereinabove, formation of stable ferrous nitrate solution can comprise dissolving iron in nitric acid having a weight percent and maintaining the solution at a first temperature for a period of time. In embodiments, the first temperature is a temperature of from about 25° C. to about 35° C. In embodiments, the first temperature is a temperature in the range of from about 30° C. to about 35° C. In embodiments, the period of time is greater than about 30 minutes. In embodiments, the period of time is greater than about 40 minutes. In embodiments, the period of time is greater than about 45 minutes. In embodiments, the nitric acid used to dissolve the iron for preparation of the stable ferrous nitrate solution is about 5 to 10 weight percent nitric acid, about 6-9 weight percent nitric acid, or about 6 weight percent nitric acid.

In embodiments, the stable ferrous nitrate solution is stable for at least one hour, at least two hours, or at least one day. In embodiments, the stable ferrous nitrate solution is stable for at least two days. In embodiments, the stable ferrous nitrate solution is stable for at least three days. In embodiments, the percent Fe(II) in the stable ferrous nitrate solution changes by less than about 1% over a period of at least about one hour, about two hours, about one day, or at least about two days. In embodiments, the percent Fe(II) in the stable ferrous nitrate solution changes by less than about 2% over a period of about one hour, about two hours, or about one day. In embodiments, the percent Fe(II) in the stable ferrous nitrate solution changes by less than about 2% over a period of about two days.

In embodiments, formation of ferric acid solution comprises dissolving iron in nitric acid having a second weight percent nitric acid and maintaining the solution at a second temperature for a period of time. In embodiments, the second temperature is a temperature in the range of from about 30° C. to about 75° C. In embodiments, the second temperature is a temperature in the range of from about 35° C. to about 75° C. In embodiments, the second temperature is a temperature of greater than about 35° C. In embodiments, the period of time is a time of greater than about 30 minutes. In embodiments, the period of time is a time of greater than about 40 minutes.

In embodiments, the period of time is a time of greater than about 45 minutes. In embodiments, the nitric acid used for dissolution of iron in preparation of ferric nitrate solution has a weight percentage of nitric acid in the range of from about 10 to about 20, in the range of from about 12 to about 18, is about 13 weight percent nitric acid, or is about 17 weight percent nitric acid.

In embodiments, forming a solution of ferric nitrate further comprises heating the ferric nitrate solution to a temperature of greater than about 70° C. In embodiments, forming a solution of ferric nitrate further comprises heating the ferric nitrate solution to a temperature of greater than about 75° C.

In embodiments, combining stable ferrous nitrate solution and ferric nitrate solution such that a stable Fe(II)/Fe(III) nitrate solution is formed having a desired ratio of ferrous to ferric iron comprises combining stable ferrous nitrate solution and ferric nitrate solution to produce a ferric/ferrous nitrate solution comprising 20 to 30 weight percent (e.g. about 25 weight percent) ferrous iron and 70 to 80 weight percent (e.g. about 75 weight percent) ferric iron. In embodiments, the percent Fe(II) in the stable Fe(II)/Fe(III) nitrate solution changes by less than about 1% over a period of about one hour, about two hours, or about one day. In embodiments, the percent Fe(II) in the stable Fe(II)/Fe(III) nitrate solution changes by less than about 2% over a period of about one hour, about two hours, or about one day. In embodiments, the percent Fe(II) in the stable Fe(II)/Fe(III) nitrate solution changes by less than about 2% over a period of about two days.

The method of forming iron catalyst can further comprise dissolving predetermined quantities of copper or at least one metalloid or metal other than iron in nitric acid to form a solution comprising cupric nitrate and/or other nitrates and precipitating a catalyst precursor comprising metal oxides by the addition of sufficient precipitating agent to the solution formed. The metal oxide comprises iron oxide selected from the group consisting of hydrous iron oxides and precipitated iron oxide, and can comprise oxides of copper, and other metal oxides. Additionally or alternatively, copper or at least one other metal or metalloid can be added following precipitation, as, for example, copper nitrate solution.

In embodiments, the method of producing the catalyst further comprises co-precipitation of at least one structural promoter with the iron of the iron catalyst. In embodiments, the catalyst comprises more than about 50 weight percent of oxides including iron oxides and other oxides. In embodiments, the metal of the mixed oxides is selected from silicon, magnesium, aluminum, copper, iron, and combinations thereof. In embodiments, the catalyst comprises up to 50 weight percent oxides selected from oxides of copper, magnesium, silicon, aluminum and combinations thereof.

In some embodiments, the catalyst comprises oxides of magnesium, copper, and aluminum in addition to iron oxides, and is formed by coprecipitation of iron with magnesium, copper, and aluminum from a nitrate solution or solutions thereof.

In some embodiments, the catalyst is formed by coprecipitation with magnesium. In embodiments, magnesium is coprecipitated from magnesium nitrate. In some embodiments, the iron catalyst is formed by coprecipitation with copper. In embodiments, copper is coprecipitated from copper nitrate. In embodiments, the iron catalyst is formed by coprecipitation with aluminum. In embodiments, aluminum is precipitated from aluminum nitrate. In some embodiments, the iron catalyst is formed by coprecipitation from aluminum nitrate. In embodiments, the iron catalyst is formed by coprecipitation of iron with magnesium, silica, aluminum, copper, or a combination thereof.

In embodiments, iron catalyst is formed by coprecipitation of iron, copper, magnesium and aluminum. In embodiments, the ratio of magnesium to aluminum atoms in the catalyst and/or in the pre-precipitation mixture is in the range of from about 0.4 to about 0.6. In embodiments, the ratio of magnesium to aluminum is about 0.5.

As discussed hereinabove, the iron FT catalyst comprises a structural promoter. In embodiments, the structural promoter comprises tetraethyl orthosilicate, TEOS. Catalyst comprising structural promoter of silica can be formed by coprecipitating the catalyst from a solution comprising TEOS structural promoter.

In embodiments, a precipitated iron catalyst is improved by adding a structural promoter to the catalyst slurry. In embodiments, the silicon-containing binder comprises potassium silicate, colloidal silica, TEOS, or a combination thereof. Without wishing to be limited by theory, adding the binder to the slurry may improve dispersion of the metals in the catalyst and/or minimize damage to particles by the addition of silica via incipient wetness method at a later stage.

In embodiments, the potassium carbonate and structural promoter are added simultaneously to precipitated catalyst precursor comprising iron, iron hydroxide, iron oxide, and/or iron carbonate. In embodiments, the structural promoter comprises silica in colloidal form. In embodiments, the silica is silica sol. In some embodiments, the silica sol is selected from TMA LUDOX, LUDOX, LUDOX AS-30 and polysilicic acid (available from Sigma Aldrich, St. Louis, Mo.).

In some embodiments, the at least one structural promoter comprises silica and the liquid structural promoter is added to the catalyst precursor (precipitated catalyst material) following the addition of potassium carbonate promoter. In embodiments, structural promoter (potassium silicate or TEOS; about 1 weight percent to 3 weight percent) is added to the precipitate comprising mixed metal oxides, hydroxides, and/or carbonates.

A spray dryer can be used to remove most of the water from the precipitated catalyst precursor and at the same time to produce roughly spherical precipitated catalyst particles having diameters in the range of 40 to 100 microns, prior to the addition of structural promoter comprising silicate via incipient wetness technique. In embodiments, a structural promoter is added to the catalyst precursor to yield a promoted mixture prior to spray drying as described above.

The catalyst can be heated in air (for example, to about 600° F.) to remove residual moisture and to stabilize the precipitated catalyst. In embodiments, this step is carried out in a fluidized bed which is heated electrically.

Following drying, the dried precipitated catalyst precursor can be calcined. In embodiments, calcination is carried out at a temperature in the range of from about 250° C. to about 450° C. In some embodiments, calcination is carried out at a temperature in the range of from about 300° C. to about 400° C. In some embodiments, calcination is performed at a temperature of about 350° C.

In embodiments, silicate structural binder is added to a calcined precipitated catalyst.

The iron catalyst can be activated prior to use in an FT process, as known to those of skill in the art. In certain embodiments, the iron catalyst is activated in situ. Many different activating procedures for promoted iron Fischer-Tropsch catalysts have been described in the literature. For example, one of the most definitive studies on activating iron Fischer-Tropsch catalysts for use in fixed-bed reactors was published by Pichler and Merkel. (United States Department of Interior Bureau of Mines, Technical Paper 718, By H. Pichler and H. Merkel, Translated by Ruth Brinkley with Preface and Foreword by L. J. E. Hofer, United States Government Printing Office, Washington, D.C., 1949, Chemical and Thermomagnetic Studies on Iron Catalysts For Synthesis of Hydrocarbons). In this study, high activity of the catalyst was correlated with the presence of iron carbides after the activation procedure. The most effective procedure used carbon monoxide at 325° C. at 0.1 atm pressure. The study also showed how the presence of copper and potassium in the catalyst affected activation of the catalyst.

In embodiments, the iron catalyst is pre-treated in hydrogen. In embodiments, the iron catalyst is pretreated with a gas comprising carbon monoxide. In embodiments, the iron catalyst is pre-treated in synthesis gas. In embodiments, pretreatment occurs at pre-selected conditions of temperature and pressure. In embodiments, these pre-selected conditions of temperature encompass a temperature of from about 250° C. to about 300° C. In embodiments, these pre-selected conditions of pressure encompass a pressure of from about 5 atm. to about 10 atm.

In embodiments, as described in U.S. Pat. No. 5,504,118, the activity and selectivity of the iron catalyst is improved by subjecting the iron catalyst to a hydrogen-rich synthesis gas at elevated temperature and pressure. The reaction of carbiding of the iron catalyst precursor using a hydrogen-rich synthesis gas and the subsequent Fischer-Tropsch reaction both produce water. Without wishing to be limited by theory, it is believed that the presence of this water prevents over-carburization of the catalyst and thereby improves the activity and selectivity of the catalyst. (See "The Influence of Water and of Alkali Promoter on the Carbon Number Distribution of Fischer-Tropsch Products Formed over Iron Catalysts" by L. Konig et al., Ber. Bunsenges. Phys. Chem. 91, 116-121 (1987)-c VHC Verlagsgesellschaft mbH, D-6940 Weinheim, 1987.)

In embodiments, hydrogen-rich synthesis gas is used in lieu of an inert gas for maintaining the iron catalyst in suspension while the slurry is being heated to approximately 200° C. At this point, the synthesis gas is replaced by an inert gas (nitrogen or carbon dioxide) until the activation temperature has been attained at which time activation is carried out using synthesis gas.

It has been reported in U.S. Pat. No. 5,504,118 that the presence of a large amount (20%) by volume of nitrogen in the synthesis gas used for pretreatment of a precipitated catalyst had no detrimental effect on the activation procedure. In embodiments, activation of the iron catalyst occurs in the presence of about 20% nitrogen.

In embodiments, the initial load of iron catalyst in a commercial-scale slurry reactor comprising several thousand pounds of catalyst is pretreated in the full-scale slurry reactor. During operation, however, when only a few hundred pounds of catalyst are to be pretreated to replace a portion of the inventory in the reactor to maintain activity, a separate pretreatment reactor may be desirable. The pretreatment reactor may be similar in design to the large Fischer-Tropsch reactor, but much smaller. The batch of slurry containing the pretreated catalyst is pumped into the large reactor as known to those of skill in the art.

In some embodiments, small amounts of iron catalyst, i.e. up to 10% by weight of the total amount of catalyst in the F-T reactor, are activated in situ by adding raw catalyst directly to the reactor at operating conditions.

In embodiments, the iron catalyst is activated by contacting the catalyst with a mixture of gaseous hydrogen and carbon monoxide at a temperature of from about 250° C. to 300° C., for about 0.5 to 5 hours, with a water vapor partial pressure of about 1 psia, and a hydrogen to carbon monoxide mol (or volume) ratio of about 0.7 to 1.5, the activation being effective to increase the selectivity of the activated iron catalyst in the subsequent formation of liquid hydrocarbons in a Fischer-Tropsch reaction. In embodiments, the syngas for activation has a $H_2$:CO mol ratio of about 1.4. In embodiments, activation in syngas occurs for a time period up to 6 hours. In embodiments, the catalyst in wax or oil is first heated to 275° C. in $H_2$ and then syngas is fed for activation.

For example, the catalyst of this disclosure can be activated using a "typhoon" activation method. According to this method, in situ catalyst activation is performed by heating the catalyst to 275° C. in nitrogen, feeding syngas at a $H_2$:CO ratio of 1.4 once attaining a temperature of 275° C., activating at 275° C. under 140 psig pressure for 4-24 hours (depending on the space velocity).

In some embodiments, iron catalyst optionally comprising support material (e.g. $MgAl_2O_4$, $MgAl_2O_4$—$SiO_2$, $Al_2O_3$, $SiO_2$, $SiO_2$—$Al_2O_3$, etc.) in oil or wax is first heated to 200° C. in $N_2$, and then syngas is fed, and the temperature is ramped to a temperature in the range of about 285° C. to 300° C. In embodiments, the syngas used for activation has a $H_2$:CO ratio of about 0.7. In embodiments, the temperature is ramped from 200° C. to a temperature of from about 285° C. to about 300° C. at a ramp rate in the range of from 1° C./min to about 5° C./min.

In some embodiments, iron catalyst according to this disclosure is activated with 100% CO.

IV. Iron FT Catalyst Formed with Stabilized Ferrous and/or Ferric/Ferrous Nitrate Solution In embodiments, depending on the pre-selected alpha, i.e., the polymerization probability desired, the precipitated iron catalyst has a weight ratio of potassium (e.g., as carbonate) to iron in the range of from about 0.005 and about 0.015, in the range of from 0.0075 to 0.0125, or about 0.010. Larger amounts of alkali metal promoter (e.g., potassium) cause the product distribution to shift toward the longer-chain molecules, while small amounts of alkali metal result in predominantly gaseous hydrocarbon product.

The weight ratio of copper to iron in the iron FT catalyst can be in the range of from about 0.005 and 0.050, in the range of from about 0.0075 and 0.0125, or about 0.010. Copper may serve as an induction promoter. In embodiments, the weight ratio of Cu:Fe is about 1:100.

As discussed in Section III hereinabove, the iron FT catalyst can further comprise structural promoter to significantly reduce the breakdown of the catalyst in a SBCR (slurry bubble column reactor). The structural promoter can comprise silica, and may enhance the structural integrity during activation and operation of the catalyst. In embodiments, the catalyst comprises a mass ratio of $SiO_2$:Fe of less than about 1:100 when the structural promoter comprises silica and less than about 8:100 when the structural promoter comprises silica sol.

In embodiments, the at least one structural promoter is selected from oxides of metals and metalloids and combinations thereof. The structural promoter may be referred to as a binder, a support material, or a structural support.

Depending on the level of structural promoter comprising silicate and the pre-selected alpha, i.e. the polymerization probability desired, the weight ratio of K:Fe is from about 0.5:100 to about 6.5:100. In embodiments, the weight ratio of K:Fe is from about 0.5:100 to about 2:100. In some embodiments, the weight ratio of K:Fe is about 1:100.

In some embodiments wherein the structural promoter comprises silica sol, the weight ratio of iron to potassium is in the range of from about 100:1 to about 100:5. In some embodiments, the weight ratio of iron to potassium is in the range of from about 100:2 to about 100:6. In embodiments, the weight ratio of iron to potassium is in the range of from about 100:3 to about 100:5. In some embodiments, the weight ratio of iron to potassium is in the range of from about 100:4 to about 100:5. In embodiments, the weight ratio of iron to potassium is in the range of from about 100:2 to about 100:4. In some specific embodiments, the weight ratio of iron to potassium about 100:3. In other certain embodiments, the weight ratio of iron to potassium about 100:5.

In some embodiments wherein the structural promoter comprises silica sol, the weight ratio of iron to copper is in the range of from about 100:1 to about 100:7. In some embodiments, the weight ratio of iron to copper is in the range of from about 100:1 to about 100:5. In embodiments, the weight ratio of iron to copper is in the range of from about 100:2 to about 100:6. In embodiments, the weight ratio of iron to copper is in the range of from about 100:3 to about 100:5. In embodiments, the weight ratio of iron to copper in the range of from about 100:2 to about 100:4. In other specific embodiments, the weight ratio of iron to copper about 100:5. In yet other specific embodiments, the weight ratio of iron to copper about 100:3.

Broadly, in embodiments, wherein the structural promoter is silica sol, the iron to $SiO_2$ weight ratio can be in the range of from about 100:1 to about 100:8; alternatively, in the range of from 100:1 to 100:7. In embodiments, wherein the structural promoter is silica, the iron to $SiO_2$ weight ratio can be in the range of from about 100:2 to about 100:6. In embodiments, the weight ratio of iron to silica is in the range of from about 100:3 to about 100:5. In embodiments, wherein the structural promoter is silica, the iron to $SiO_2$ weight ratio is about 100:5. In embodiments, wherein the structural promoter is silica, the iron to $SiO_2$ weight ratio can be in the range of from about 100:3 to about 100:7; alternatively, in the range of from about 100:4 to about 100:6.

In embodiments, the $Fe:Cu:K:SiO_2$ mass ratio is about 100:4:3:5.

During FT conversion, the percent by weight of the disclosed iron catalyst in the reactor slurry (for example, in a slurry bubble column reactor, or SBCR) can be in the range of from 5 to 15 percent by weight of iron in the slurry, in the range of from about 7.5 to 12.5 percent by weight of iron in the slurry, or about 10 percent by weight of the slurry.

V. Examples

A. Example 1

Stability of Ferrous Nitrate Solutions, Ferric Nitrate Solutions, and Fe(II)/Fe(III) Nitrate Solutions. Iron powder (Hoeganaes) and nitric acid (VWR, 68-70%) were used to make (1) ferrous nitrate, (2) ferric nitrate and (3) 25% ferrous/75% ferric nitrate solutions. The pH of each solution was measured at room temperature on a regular basis, to study stability.

Preparation of Ferrous Nitrate (Fe(II) Nitrate) Solution (1):

Ferrous nitrate solution (1) was prepared by dissolving iron powder in nitric acid of specific gravity of 1.03122, which corresponds to nitric acid of 6 weight percent, in an ice bath. The color of the solution was dark green.

Preparation of Ferric Nitrate (Fe(III) Nitrate) Solution (2):

Ferric nitrate solution (2) was prepared by dissolving iron powder in nitric acid of specific gravity of 1.1469, which corresponds to nitric acid of 25 weight percent, in an ice bath. The color of the solution was green.

Preparation of Ferrous (25 w %)/Ferric Nitrate (75 w %) Solution (Fe(II)/Fe(III) Cold; 3a):

For the production of ferrous (25 w %)/ferric nitrate (75 w %) solution (Cold; 3a), appropriate amounts of ferrous (1) and ferric nitrate (2) solutions were mixed at room temperature. The color of the solution was green.

Preparation of Ferrous (25 w %)/Ferric Nitrate (75 w %) Solution (Fe(II)/Fe(III) Hot; 3b):

To ensure that all iron in the ferric solution (2) was ferric, for the preparation of ferrous (25 weight percent)/ferric nitrate (75%) solution (Hot; 3b), ferric nitrate solution (2) was heated to 65° C. prior to mixing with ferrous nitrate solution (1) at room temperature. The heated Fe(III) solution (2) became red while nitric oxide was given off. The color of the combined Fe(II)/Fe(III) solution was green.

The pH of each nitrate solution was measured and listed in Table 1. While the pH of each nitrate solution changed, the color of the solutions also slowly changed to red from green in about a week. The color change was gradual, and difficult to observe visually.

Figure 1:
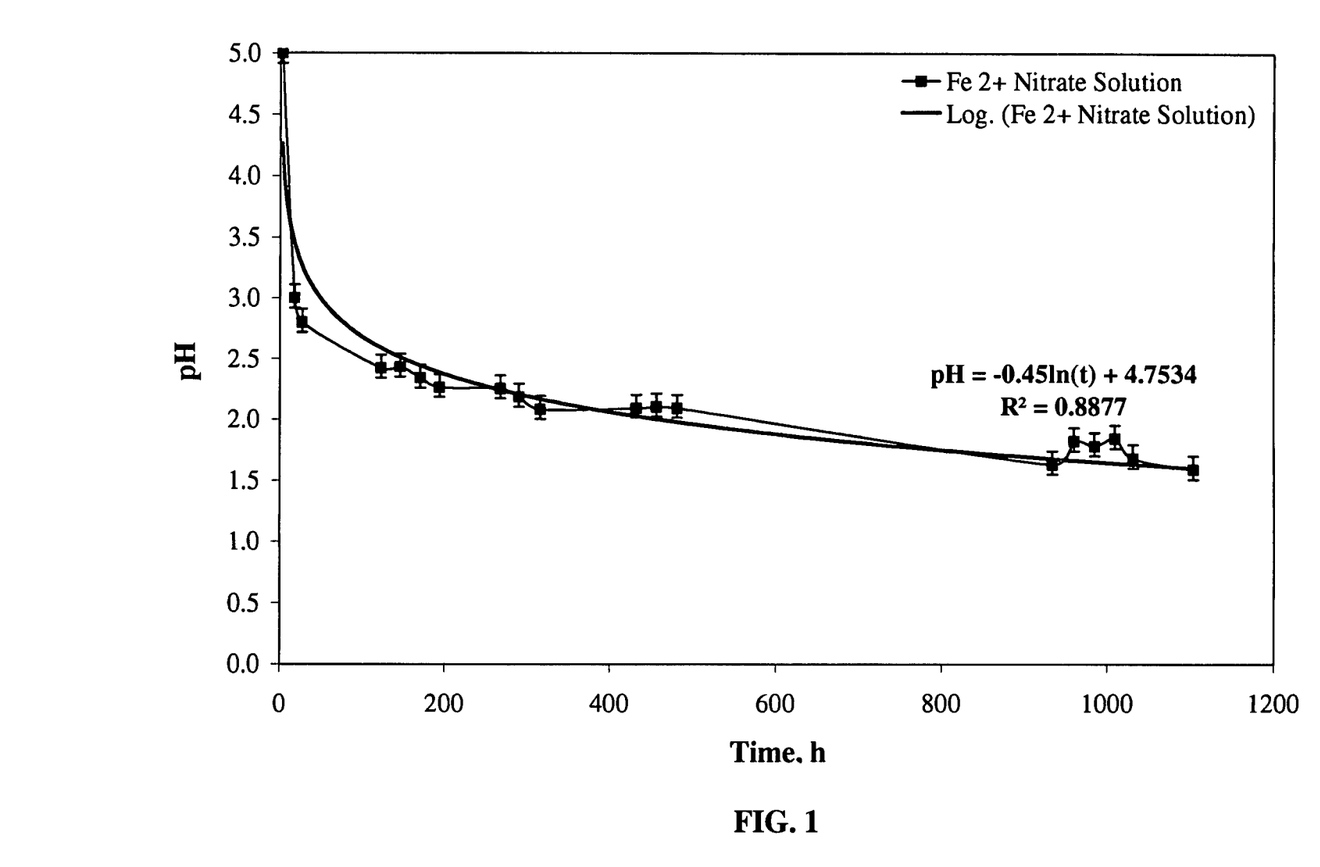
FIG. 1 is a plot of pH of ferrous nitrate solution as a function of time.

Yellow sediments were observed in the bottom of the ferrous nitrate (Fe(II) Nitrate) solution (1) in less than 24 hours. The results from this experiment shows that ferrous iron tends to oxidize to ferric iron while pH changes from 5 to about 1.6. This is expected because the solution becomes more acidic due to gradual evolution of nitric acid during the conversion of ferrous nitrate to ferric iron oxide according to Equation (2) hereinabove. FIG. 1 is a plot of pH of ferrous nitrate solution (1) as a function of time. The change in pH was initially quite rapid, and slowed down at lower pH values (see FIG. 1).

Figure 2:
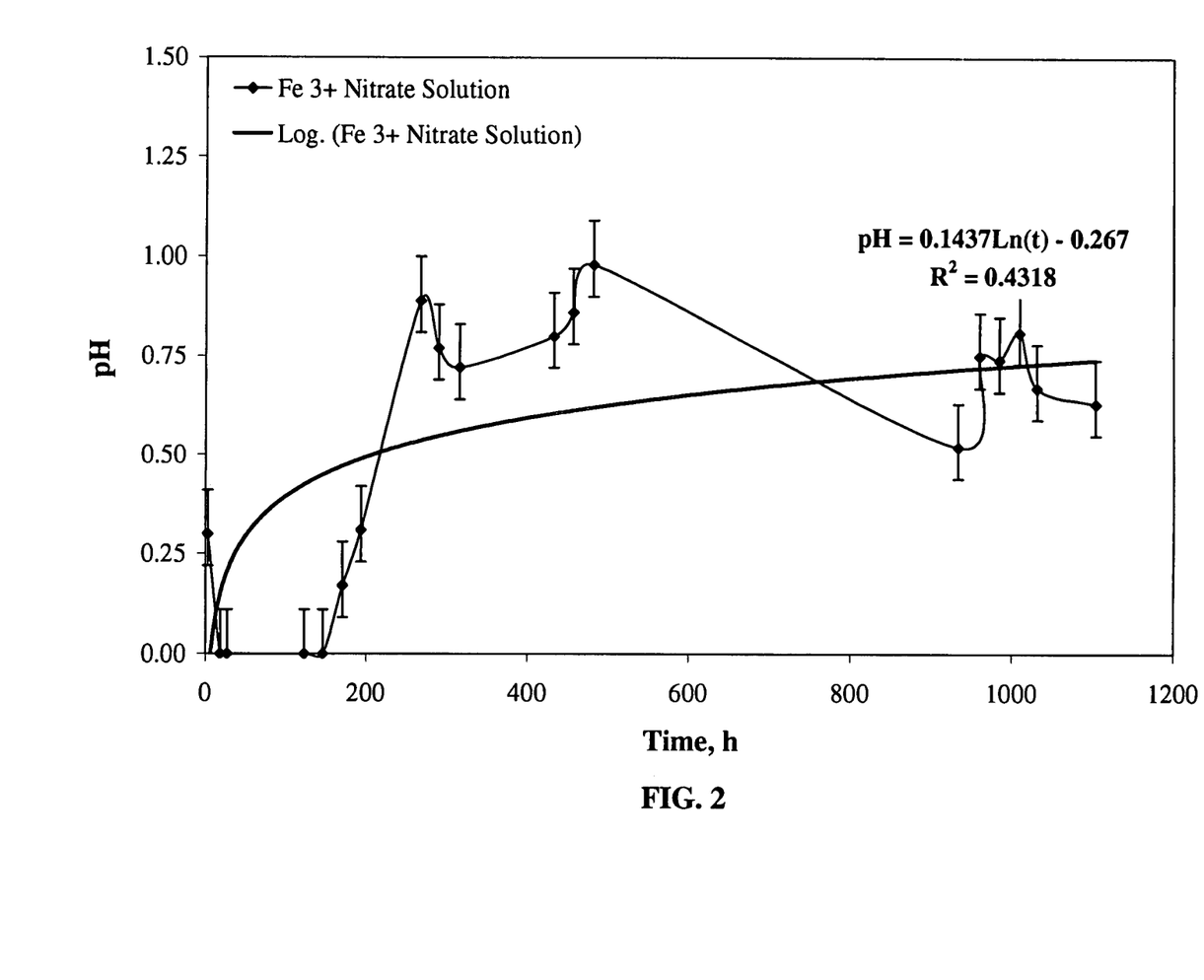
FIG. 2 is a plot of pH of ferric nitrate solution as a function of time.

FIG. 2 is a plot of plot of pH of ferric nitrate solution (2) as a function of time. As seen in FIG. 2, the pH of Fe(III) nitrate solution was very close to zero and remained steady for about a week. The color of the ferric nitrate solution (2) changed to red from green with time. This may be explained by ionic equilibrium in the solution.

Figure 3:
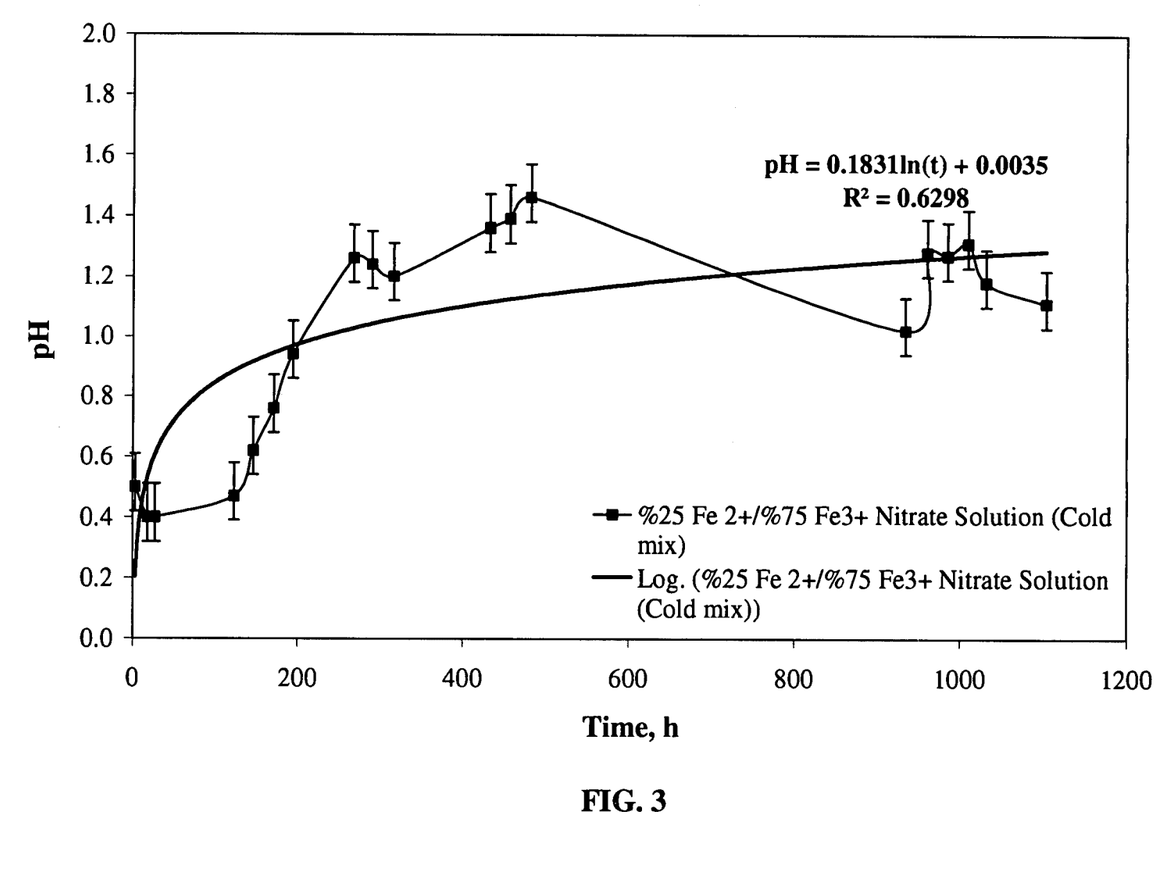
FIG. 3 is a plot of pH as a function of time for a solution containing 25% ferrous/75% ferric nitrate (cold).

FIG. 3 is a plot of pH as a function of time for 25% ferrous/75% ferric nitrate solution (cold), 3a. The ferrous (25 weight percent)/ferric nitrate (75 weight percent) solution 3a (Fe(II)/Fe(III) Cold) also exhibited a change in pH with time. The color of Fe(II)/Fe(III) nitrate solution 3a changed from green to red with time. No sedimentation was observed. Ferric nitrate alone is formed in nitric acid of specific gravity of 1.115 and higher. The specific gravity of this solution was calculated 1.1179. The ferrous nitrate in the solution 3a was converted to ferric nitrate without any precipitation.

Figure 4:
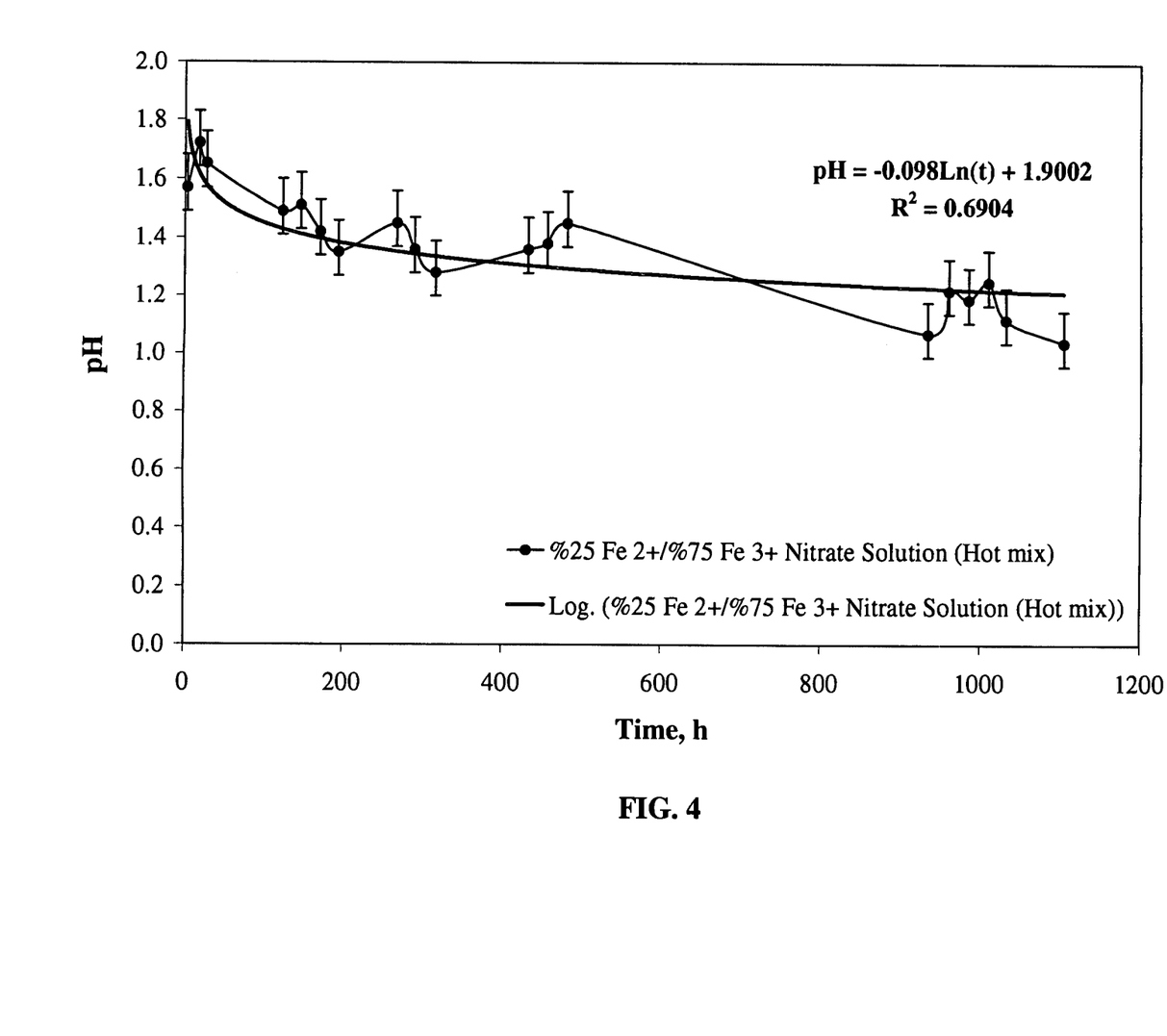
FIG. 4 is a plot of pH as a function of time for a solution containing 25% ferrous/75% ferric nitrate (hot).

FIG. 4 is a plot of pH as a function of time for 25% ferrous/75% ferric nitrate solution (hot), 3b. Ferrous (25 w %)/ferric nitrate (75 w %) solution 3b (Fe(II)/Fe(III) Hot) exhibited changes in pH from about 1.5 initially to about 1 after about 800 hours. This may be due to the formation of nitric acid during oxidation reactions. Precipitation of ferric oxide was observed after the first 300 hours and slowly increased with time. Without wishing to be limited by theory, heating ferric nitrate solution (2) prior to mixing ferrous nitrate solution (1) and ferric nitrate solutions (2) may have created a media from which ferric hydroxide can be formed by hydrolysis reaction (see Equation (3) hereinabove). The hydrolysis reaction (3) is dependent on concentration, time, temperature, acidity and the presence of other substances in the solution. Completion of oxidation reaction at lower pH takes a longer time, and ferric oxide deposits were formed more slowly in solution 3b at lower pH relative to the deposition of ferric oxide deposits from the Fe(II) nitrate solution (2) which was at higher pH.

TABLE 1 pH Values of Nitrate Solutions

| Time, h | pH | | | |
|---|---|---|---|---|
| | Fe(II) Nitrate | Fe(III) Nitrate | Fe(II)/Fe(III) Cold | Fe(II)/Fe(III) Hot |
| 3.00 | 5 | 0.3 | 0.5 | 1.57 |
| 18.00 | 3[1] | 0 | 0.4 | 1.72 |
| 27.00 | 2.8 | 0 | 0.4 | 1.65 |
| 126.00 | 2.42 | 0 | 0.47 | 1.49[1] |
| 149.00 | 2.43 | 0 | 0.62 | 1.51 |
| 173.50 | 2.34 | 0.17 | 0.76 | 1.42 |
| 196.50 | 2.26 | 0.31 | 0.94 | 1.35 |
| 270.25 | 2.25 | 0.89 | 1.26 | 1.45 |
| 292.50 | 2.18 | 0.77 | 1.24 | 1.36 |
| 318.50[2] | 2.08 | 0.72 | 1.2 | 1.28 |
| 434.75 | 2.09 | 0.8 | 1.36 | 1.36 |
| 458.75 | 2.1 | 0.86 | 1.39 | 1.38 |
| 483.75 | 2.09 | 0.98 | 1.46 | 1.45 |
| 937.00 | 1.63 | 0.52 | 1.02 | 1.07 |
| 963.50 | 1.82 | 0.75 | 1.28 | 1.22 |
| 988.00 | 1.78 | 0.74 | 1.27 | 1.19 |
| 1013.00 | 1.84 | 0.81 | 1.31 | 1.25 |
| 1034.50 | 1.68 | 0.67 | 1.18 | 1.12 |
| 1106.75 | 1.59 | 0.63 | 1.11 | 1.04 |

[1]Sediments observed in bottom of solution bottle.
[2]Color of solutions changed to red.

B. Example 2

Stability of Fe(II)/Fe(III) Mixtures

Further experiments were performed to understand the factors that affect Fe(II) stability in mixed Fe(II)/Fe(III) solutions. During these experiments, it was found that the reproducibility of the Fe(II) measurements was greatly increased from ±5% to ±0.5% by excessive rinsing of the sample cells.

1. AR60-01.

Solutions of ferrous nitrate (1) and ferric nitrate (2) were formed. Ferrous nitrate solution (1) was formed by combining iron metal with nitric acid at 35° C. and holding at that temperature for 10 minutes. Ferric nitrate solution (2) was formed by combining iron metal with nitric acid at 35° C. and holding at that temperature for 10 minutes and then heating to 70° C. for 30-40 minutes. The solutions were mixed to form a solution with 10% Fe(II). Ferrous nitrate solution (1) and ferric nitrate solution (2) were not filtered in this experiment, and were not covered during iron dissolution/heating. The pH of the solutions was monitored over a period of four days, as indicated in Table 2.

TABLE 2

AR60-01

| | | Fe(II) Solution | | | Fe(II)/(III) Solution | | |
|---|---|---|---|---|---|---|---|
| Day | Time | Fe(II) | Fe[r] | % Fe(II) | Fe(II) | Fe[r] | % Fe(II) |
| 1 | 13:00 | 1.78 | 1.85 | 96.2 | 0.16 | 1.68 | 9.5 |
| 1 | 14:00 | 2.02 | 2.10 | 96.2 | 0.19 | 1.78 | 10.7 |
| 1 | 15:00 | 2.05 | 2.13 | 96.2 | 0.19 | 1.80 | 10.6 |
| 1 | 15:00 | 2.02 | 2.04 | 99.0 | 0.22 | 1.54 | 14.3 |
| 1 | 16:00 | 2.18 | 2.22 | 98.2 | 0.23 | 1.58 | 14.6 |
| 1 | 16:00 | 2.20 | 2.18 | 100.9 | 0.19 | 1.91 | 9.9 |
| 2 | 9:00 | 1.72 | 1.82 | 94.5 | 0.22 | 2.14 | 10.3 |

TABLE 2-continued

AR60-01

| | | Fe(II) Solution | | | Fe(II)/(III) Solution | | |
|---|---|---|---|---|---|---|---|
| Day | Time | Fe(II) | Fe[r] | % Fe(II) | Fe(II) | Fe[r] | % Fe(II) |
| 3 | 8:00 | 2.12 | 2.70 | 78.5 | 0.23 | 1.69 | 13.6 |
| 3 | 15:00 | — | — | — | 0.35 | 2.62 | 13.4 |
| 4 | — | — | — | — | 0.32 | 2.54 | 12.6 |

Fe[r] = Fe total = Fe(II) + Fe(III)

It appears from the data presented in Table 2 that, on a laboratory scale, having the containers holding ferrous nitrate solution (1) and ferric nitrate solution (2) uncovered results in volume loss over time; this appears to result in an initial slight increase in Fe(II) concentration. The resulting increase in nitric acid concentration leads to oxidization of Fe(II) to Fe(III). The Fe(II) content in both the ferrous nitrate solution (1) and the ferric nitrate solution (2) is stable for 2 days using this method.

2. AR60-02.

Solutions of ferrous nitrate (1) and ferric nitrate (2) were formed as described in V.B.1 hereinabove. Ferric/ferrous nitrate solution 3b (hot) was formed by combining appropriate amounts of ferrous nitrate solution (1) and ferric nitrate solution (2), with the ferric nitrate solution (2) being heated to a temperature of 70° C. for 40 minutes prior to combination with ferrous nitrate solution (1) and formation of Fe(II)/Fe (III) nitrate solution 3b (hot). Again, the individual ferrous and ferric solutions were maintained at 35° C. for 10 minutes. In this experiment, ferric nitrate solution (2) was not filtered, while the ferrous nitrate solution (1) was filtered. Again, the solutions were not covered. The pH of the solutions was measured as indicated in Table 2b.

TABLE 2b

AR60-02

| Fe(II) Solution | | | Fe(II)/Fe(III) Solution | | | Fe(III) Solution | | |
|---|---|---|---|---|---|---|---|---|
| Fe(II) | Fe[r] | % Fe(II) | Fe(II) | Fe[r] | % Fe(II) | Fe(II) | Fe[r] | % Fe(II) |
| 1.73 | 1.76 | 98.3 | 1.77 | 2.44 | 72.5 | 1.76 | 2.52 | 69.8 |

Fe[r] = Fe total = Fe(II) + Fe(III)

In this experiment, either the Fe(III) solution did not fully oxidize by heating to 70° C. for 40 minutes, or the iron that was not filtered away was oxidized to Fe(II) during cooling. It appears that ferric/ferrous nitrate solution (3b) (hot) can be beneficially heated at 30° C. for longer than 10 minutes.

3. AR60-03.

Solutions of ferrous nitrate (1), ferric nitrate (2), and ferric/ferrous nitrate (3) were formed as described in V.B.1 hereinabove. In this experiment, the individual ferrous and ferric solutions (1 and 2) were maintained at 35° C. for 45 minutes. The ferric nitrate solution (3) was heated to 70° C. for 40 min. In this experiment, ferric nitrate solution (2) was slightly filtered upon cooling, but not prior to heating. Ferrous nitrate solution (1) was filtered. In this experiment, the solutions were covered.

The pH of the solutions was measured as indicated in Table 3.

TABLE 3

| | | | | AR60-03, AR60-04 | | | | | |
|---|---|---|---|---|---|---|---|---|---|
| Day | Time | Fe(II) | Fe$^t$ | % Fe(II) | Fe(II) | Fe$^t$ | % Fe(II) | Fe(II) | Fe$^t$ | % Fe(II) |
| AR 60-03 | | Fe(II) Solution | | | Fe(II)/Fe(III) Solution* | | | Fe(III) Solution | | |
| 1 | 14.30 | 1.70 | 1.74 | 97.7 | 0.14 | 1.60 | 8.8 | 0.04 | 1.95 | 2.1 |
| 2 | 9.30 | 1.65 | 1.74 | 94.8 | 0.19 | 2.07 | 9.2 | 0.11 | 2.07 | 5.3 |
| 3 | 9.00 | 1.68 | 1.78 | 94.4 | 0.04 | 2.10 | 1.9 | 0.09 | 1.74 | 5.2 |
| AR 60-04 | | Fe(II) Solution | | | Fe(II)/Fe(III) Solution | | | Fe(III) Solution | | |
| 1 | 14:30 | 1.69 | 1.76 | 96.0 | 0.17 | 2.09 | 8.1 | 0.03 | 2.68 | 1.1 |
| 1 | 14:45 | — | — | — | 0.19 | 2.16 | 8.8 | — | — | — |
| 1 | 15:00 | — | — | — | 0.26 | 3.03 | 8.6 | — | — | — |
| 1 | 15:45 | — | — | — | 0.19 | 2.25 | 8.4 | — | — | — |
| 1 | 16:30 | — | — | — | 0.21 | 2.39 | 8.8 | — | — | — |
| 3 | 7:30 | 0.37 | 1.63 | 22.7 | 0.03 | 2.00 | 1.5 | 0.03 | 2.43 | 1.2 |

Fe$^t$ = Fe total = Fe(II) + Fe(III)
*There was interruption of the stirring of the Fe(II)/Fe(III) solution at some point between day 1 and day 2.

From the data in Table 3, it appears that the Fe(II) content may increase in the Fe(III) solution if the elemental iron is not filtered following the addition of acid. The Fe(II) content in the Fe(II)/Fe(III) solution was stable for up to 1 day and may have been stable for longer if stirring had not been inadvertently interrupted.

4. AR60-04.

Solutions of ferrous nitrate (1), ferric nitrate (2), and ferric/ferrous nitrate (3) were formed as described in V.B.1 hereinabove. In this experiment, the individual ferrous and ferric solutions (1 and 2) were maintained at 35° C. for 45 minutes. In this experiment, both Fe(III) and Fe(II) solutions were filtered after acid addition. The ferric nitrate (3) solution was heated to 70° C. for 40 min. In this experiment, the solutions were covered. The final Fe(II)/Fe(III) nitrate solution was maroon brown in color.

The pH of the solutions was measured as indicated in Table 3. The stability of Fe(II) is high for the first hour in the mixture if elemental iron is removed from the system. The long term stability of Fe(II) is reduced compared to AR60-03.

5. AR60-05.

Solutions of ferrous nitrate (1), ferric nitrate (2), and ferric/ferrous nitrate (3) were formed as described in V.B.1 hereinabove. In this experiment, the individual ferrous and ferric solutions (1 and 2) were maintained at 30-34° C. during acid addition. The ferrous nitrate solution (1) and ferric nitrate solution (2) were maintained at 35° C. for 45 minutes. The experiment was performed in quadruplicate. The solutions were filtered after acid addition. The solutions were then divided, with 90% to be heated and 10% to remain at 30° C. In this experiment, the solutions were covered. The final ferric/ferrous nitrate solution was light orange-brown in color.

The Fe(II) concentrations of the solutions as measured are indicated in Table 4. Measurements were performed in triplicate.

TABLE 4

| | | | | | AR60-05 | | | | | | | |
|---|---|---|---|---|---|---|---|---|---|---|---|---|
| | | | | | Fe(II)/Fe(III) Solution | | | | | | Avg. | Std. |
| Day | Time | Fe(II) | Fe$^t$ | % Fe(II) | Fe(II) | Fe$^t$ | % Fe(II) | Fe(II) | Fe$^t$ | % Fe(II) | % Fe(II) | Dev. |
| 1 | 14.25 | 0.18 | 1.72 | 10.5 | 0.19 | 1.87 | 10.2 | 0.30 | 1.55 | 19.4 | 13.3** | 5.2 |
| 1 | 14.40 | 0.16 | 1.66 | 9.6 | 0.30 | 1.67 | 18.0 | 0.27 | 1.62 | 16.7 | 14.8** | 4.5 |
| 1 | 14.55 | 0.16 | 1.72 | 9.3 | 0.16 | 1.65 | 9.7 | 0.13 | 1.44 | 9.0 | 9.3 | 0.3 |
| 1 | 15.10 | 0.17 | 1.79 | 9.5 | 0.17 | 1.69 | 10.1 | 0.18 | 1.83 | 9.8 | 9.8 | 0.3 |
| 2 | 9.05 | 0.12 | 1.80 | 6.7 | 0.13 | 1.82 | 7.1 | 0.12 | 1.88 | 6.4 | 6.7 | 0.4 |
| 2 | 16.45 | 0.05 | 1.35 | 3.7 | — | — | — | — | — | — | — | — |
| 5 | 9.00 | 0.01 | 1.74 | 0.6 | — | — | — | — | — | — | — | — |

| | | Fe(II) Solution | | | Fe(III) Solution | | |
|---|---|---|---|---|---|---|---|
| | Day | Time | Fe(II) | Fe$^t$ | % Fe(II) | Fe(II) | Fe$^t$ | % Fe(II) |
| | 1 | 14.25 | 1.83 | 1.85 | 98.9 | 0.02 | 1.26 | 1.6 |
| | 1 | 14.40 | 1.85 | 1.88 | 98.4 | 0.02 | 1.24 | 1.6 |
| | 1 | 14.55 | 1.89 | 1.94 | 97.4 | — | — | — |
| | 1 | 15.10 | 1.80 | 1.84 | 97.8 | — | — | — |

Fe$^t$ = Fe total = Fe(II) + Fe(III)

From the data in Table 4, it appears that the Fe(II) content in the mixed Fe(II)/Fe(III) solution is stable for a least one hour using this preparation.

6. AR60-06.

For this experiment, iron was dissolved using 17.5% $HNO_3$ for both the ferric nitrate solution (2) and the ferric nitrate solution (1). Both ferrous nitrate solution (1) and ferric nitrate solution (2) were held at 35° C. for 45 minutes for dissolution. The solutions were then cooled and filtered. The ferric nitrate solution (2) was heated to 70° C. for 40 min. The ferrous/ferric nitrate solution (3) was formed as described herein. Results are presented in Table 5.

TABLE 5

AR60-06, Stability Study

| Time, | Fe(II) Solution | | | Fe(III) Solution | | | Fe(III)/Fe(II) Solution | | |
|---|---|---|---|---|---|---|---|---|---|
| hr | Fe(II) | $Fe^{Total}$ | % Fe(II) | Fe(II) | $Fe^{Total}$ | % Fe(II) | Fe(II) | $Fe^{Total}$ | % Fe(II) |
| 0.0 | 2.28 | 2.30 | 99.1 | 0.04 | 2.29 | 1.7 | 0.21 | 2.30 | 9.1 |
| 0.5 | 1.91 | 1.93 | 99.0 | 0.04 | 2.46 | 1.6 | 0.18 | 2.35 | 7.7 |
| 1.0 | 1.84 | 1.87 | 98.4 | 0.03 | 2.29 | 1.3 | 0.18 | 2.26 | 8.0 |
| 3.5 | 1.73 | 1.76 | 98.3 | 0.03 | 2.34 | 1.3 | 0.18 | 2.35 | 7.7 |
| 20.5 | 1.56 | 1.64 | 95.1 | 0.00 | 2.59 | 0.0 | 0.01 | 2.11 | 0.5 |
| 27.5 | 1.76 | 1.87 | 94.1 | — | — | — | — | — | — |
| 45.5 | 1.89 | 2.56 | 73.8 | — | — | — | — | — | — |
| 51.5 | 1.55 | 2.69 | 57.6 | — | — | — | — | — | — |
| 69.5 | 0.66 | 2.20 | 30.0 | — | — | — | — | — | — |
| 75.5 | 0.50 | 2.09 | 23.9 | — | — | — | — | — | — |
| 93.5 | 0.19 | 1.95 | 9.7 | — | — | — | — | — | — |
| 99.0 | 0.05 | 207 | 2.4 | — | — | — | — | — | — |

Fe(II) containing solutions appear to be stable for the first few hours by this method.

7. AR60-07.

For this experiment, iron was dissolved in 17.5% $HNO_3$ for both Fe(III) and Fe(II) solutions. Both solutions were held at 35° C. for 45 minutes. The solutions were not filtered for this experiment. The data are presented in Table 6.

TABLE 6

AR60-07, Stability Study

| Time, | Fe(II) Solution | | | Fe(III) Solution | | | Fe(III)/Fe(II) Solution | | |
|---|---|---|---|---|---|---|---|---|---|
| hr | Fe(II) | $Fe^{Total}$ | % Fe(II) | Fe(II) | $Fe^{Total}$ | % Fe(II) | Fe(II) | $Fe^{Total}$ | % Fe(II) |
| 0.0 | 1.67 | 1.70 | 98.2 | 0.00 | 1.98 | 0.0 | 0.13 | 1.91 | 6.8 |
| 1.0 | 1.76 | 1.80 | 97.8 | 0.00 | 2.05 | 0.0 | 0.14 | 2.16 | 6.5 |
| 2.0 | 1.80 | 1.85 | 97.3 | 0.00 | 2.09 | 0.0 | 0.13 | 2.17 | 6.0 |
| 19.5 | 1.68 | 1.86 | 90.3 | 0.00 | 2.34 | 0.0 | 0.00 | 2.49 | 0.0 |
| 26.0 | 1.50 | 1.75 | 85.7 | — | — | — | — | — | — |
| 44.0 | 1.10 | 1.84 | 59.8 | — | — | — | — | — | — |
| 50.0 | 0.87 | 1.78 | 48.9 | — | — | — | — | — | — |
| 68.0 | 0.05 | 1.70 | 2.9 | — | — | — | — | — | — |
| 73.5 | 0.01 | 1.90 | 0.5 | — | — | — | — | — | — |

The Fe(II) containing solutions were stable for the first couple of hours as shown in Table 6.

8. AR60-08.

For experiments AR60-08, AR60-09, and AR60-10, a lower temperature of 25° C. was maintained during the addition of nitric acid. For experiment AR60-08, iron was dissolved in 17.5% $HNO_3$ for both Fe(III) and Fe(II), and the solutions were held at 25° C. for 45 minutes. As with AR60-07, the ferrous nitrate and ferric nitrate solutions were not filtered. The results are presented in Table 7.

TABLE 7

| | AR60-08, Stability Study | | | | | | | | |
|---|---|---|---|---|---|---|---|---|---|
| Time, | Fe(II) Solution | | | Fe(III) Solution | | | Fe(III)/Fe(II) Solution | | |
| hr | Fe(II) | Fe$^{Total}$ | % Fe(II) | Fe(II) | Fe$^{Total}$ | % Fe(II) | Fe(II) | Fe$^{Total}$ | % Fe(II) |
| 0.0 | 1.87 | 1.90 | 98.4 | 0.00 | 2.14 | 0.0 | 0.20 | 2.35 | 8.5 |
| 1.0 | 1.80 | 1.85 | 97.3 | 0.01 | 2.15 | 0.5 | 0.16 | 1.92 | 8.3 |
| 18.0 | 1.38 | 1.96 | 70.4 | 0.00 | 2.23 | 0.0 | 0.01 | 2.24 | 0.4 |

As seen in the data presented in Table 7, the Fe(II)-containing solutions were stable for the first hour, but not overnight.

9. AR60-09.

For this experiment, iron was dissolved in 17.5% HNO$_3$ for both Fe(III) and Fe(II). Both solutions were held at 25° C. for 45 minutes. In this experiment, both ferrous nitrate and ferric nitrate solutions were filtered after acid addition. The results are presented in Table 8.

TABLE 8

| | AR60-09, Stability Study | | | | | | | | |
|---|---|---|---|---|---|---|---|---|---|
| Time, | Fe(II) Solution | | | Fe(III) Solution | | | Fe(III)/Fe(II) Solution | | |
| hr | Fe(II) | Fe$^{Total}$ | % Fe(II) | Fe(II) | Fe$^{Total}$ | % Fe(II) | Fe(II) | Fe$^{Total}$ | % Fe(II) |
| 0.0 | 1.91 | 1.94 | 98.5 | 0.01 | 1.99 | 0.5 | 0.15 | 1.86 | 8.1 |
| 1.0 | 2.34 | 2.39 | 97.9 | 0.00 | 2.16 | 0.0 | 0.14 | 1.86 | 7.5 |
| 17.5 | 1.48 | 1.88 | 78.7 | 0.02 | 2.36 | 0.8 | 0.00 | 2.21 | 0.0 |

As seen in the data presented in Table 8, the Fe(II)/Fe(III) solution was stable for at least one hour, but did not exhibit overnight stability.

10. AR60-10.

For this experiment, iron was dissolved in 6% HNO$_3$ for the Fe(II) solution, while iron was dissolved in 28% HNO$_3$ for the Fe(III) solution. Both solutions were held at 25° C. for 45 minutes, and both solutions were filtered after acid addition. Results of this experiment are presented in Table 9.

TABLE 9

| | AR60-9, Stability Study | | | | | | | | |
|---|---|---|---|---|---|---|---|---|---|
| Time, | Fe(II) Solution | | | Fe(III) Solution | | | Fe(III)/Fe(II) Solution | | |
| hr | Fe(II) | Fe$^{Total}$ | % Fe(II) | Fe(II) | Fe$^{Total}$ | % Fe(II) | Fe(II) | Fe$^{Total}$ | % Fe(II) |
| 0.0 | 0.69 | 0.71 | 97.2 | 0.03 | 3.30 | 0.9 | 0.24 | 3.17 | 7.6 |
| 1.0 | 0.71 | 0.73 | 97.3 | 0.03 | 2.61 | 1.1 | 0.23 | 2.78 | 8.3 |
| 2.0 | 0.68 | 0.71 | 95.8 | 0.03 | 3.30 | 0.9 | 0.20 | 2.64 | 7.6 |
| 18.5 | 0.60 | 0.66 | 90.9 | 0.04 | 3.30 | 1.2 | 0.02 | 1.92 | 1.0 |
| 26.5 | 0.68 | 0.75 | 90.7 | — | — | — | — | — | — |
| 44.0 | 0.65 | 0.72 | 90.3 | — | — | — | — | — | — |
| 67.5 | 0.67 | 0.76 | 88.2 | — | — | — | — | — | — |
| 143.5 | 0.35 | 0.70 | 50.0 | — | — | — | — | — | — |

As seen in the data presented in Table 9, good stability is shown for the Fe(III)/Fe(II) mixture for the first 2 hours using this method. It is appears that using only 6% nitric acid for the production of ferrous nitrate solution (1) may increase the stability of the Fe(II) solutions.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A method of producing a stable Fe(II)/Fe(III) nitrate solution comprising ferrous nitrate and ferric nitrate and having a desired ratio of ferrous iron to ferric iron, the method comprising:

obtaining a stable ferrous nitrate solution by dissolving iron in a nitric acid solution consisting of aqueous nitric acid having a first nitric acid concentration to form a ferrous nitrate solution and maintaining the solution at a first emperature for a first time period greater than thirty minutes;

dissolving iron in nitric acid having a second nitric acid concentration to form a ferric nitrate solution, wherein the second nitric acid concentration is greater than the first nitric acid concentration;

maintaining the ferric nitrate solution at a second temperature; and combining amounts of stable ferrous nitrate solution and ferric nitrate solution to produce the stable Fe(II)/Fe(III) nitrate solution having the desired ratio of ferrous iron to ferric iron, wherein the Fe(II) content of the stable Fe(II)/Fe(III) nitrate solution changes by less than about 2 weight percent over a time period of at least one day.

2. The method of claim 1 wherein the first nitric acid concentration is in the range of from about 5 to about 10 weight percent.

3. The method of claim 1 wherein the first temperature is a temperature in the range of from about 25° C. to about 35° C.

4. The method of claim 1 further comprising covering the ferrous nitrate solution during the first time period.

5. The method of claim 1 wherein the Fe(II) content of the ferrous nitrate solution changes by less than about 2 weight percent over a time period of greater than one hour.

6. The method of claim 5 wherein the Fe(II) content of the ferrous nitrate solution changes by less than about 2 weight percent over a time period of at least one day.

7. The method of claim 1 wherein the nitric acid having a second nitric acid concentration has a specific gravity of greater than 1.115.

8. The method of claim 1 further comprising heating the ferric nitrate solution to a third temperature, wherein the third temperature is greater than the first temperature.

9. The method of claim 1 further comprising covering the ferric nitrate solution prior to combining amounts of stable ferrous nitrate solution and ferric nitrate solution.

10. The method of claim 1 wherein the desired ratio of ferrous iron to ferric iron is about 1:3.

11. The method of claim 1 further comprising allowing the stable ferrous nitrate solution to cool to room temperature prior to combining amounts of stable ferrous nitrate solution and ferric nitrate solution to produce the stable Fe(II)/Fe(III) nitrate solution.

12. The method of claim 1 further comprising filtering the ferrous nitrate solution, the ferric nitrate solution, or both.

13. A method of producing an iron catalyst, the method comprising:

obtaining a stable Fe(II)/Fe(III) nitrate solution according to claim 1; and combining the stable Fe(II)/Fe(III) nitrate solution with a precipitating agent whereby catalyst precipitate is formed.

14. The method of claim 13 wherein the stable Fe(II)/Fe(III) nitrate solution has a desired ratio of ferrous iron to ferric iron of about 1:3.

15. The method of claim 13 wherein the precipitating agent is selected from the group consisting of $NH_4OH$, $(NH_4)_2CO_3$, $NH_4HCO_3$, $NaOH$, $Na_2CO_3$, $NaHCO_3$, $KOH$, $K_2CO_3$, $KHCO_3$, and combinations thereof.

16. The method of claim 13 further comprising co-precipitating at least one other metal or metalloid from a nitrate solution.

17. The method of claim 16 wherein the at least one other metal or metalloid is selected from the group consisting of magnesium, copper, aluminum, silicon, and combinations thereof.

18. The method of claim 13 further comprising washing the precipitate.

19. The method of claim 18 further comprising alkalizing the precipitate with an alkaline material.

20. The method of claim 13 further comprising promoting the precipitate by contacting the precipitate with a structural promoter.

21. The method of claim 20 wherein the structural promoter comprises liquid potassium silicate, tetraethyl ortho silicate, or a combination thereof.

* * * * *